United States Patent
Saito et al.

(10) Patent No.: US 8,358,735 B2
(45) Date of Patent: *Jan. 22, 2013

(54) TEST METHOD AND TEST DEVICE

(75) Inventors: Junichi Saito, Tokyo (JP); Hailong Cui, Tokyo (JP)

(73) Assignee: Toppan Printing Co., Ltd. (JP)

( * ) Notice: Subject to any disclaimer, the term of this patent is extended or adjusted under 35 U.S.C. 154(b) by 273 days.

This patent is subject to a terminal disclaimer.

(21) Appl. No.: 12/939,382

(22) Filed: Nov. 4, 2010

(65) Prior Publication Data

US 2011/0080998 A1  Apr. 7, 2011

Related U.S. Application Data

(63) Continuation of application No. 12/625,174, filed on Nov. 24, 2009, now Pat. No. 7,852,982, which is a continuation of application No. PCT/JP2008/052560, filed on Feb. 15, 2008.

(30) Foreign Application Priority Data

Jan. 21, 2008 (JP) .................................. 2008-010300
Feb. 15, 2008 (JP) .................................. 2008-531053

(51) Int. Cl.
 *G01N 23/223* (2006.01)
(52) U.S. Cl. ........................................... 378/50; 378/44
(58) Field of Classification Search .................... 378/57, 378/58, 454, 46; 356/237.1, 237, 2, 237.3
See application file for complete search history.

(56) References Cited

U.S. PATENT DOCUMENTS

| | | | | |
|---|---|---|---|---|
| 5,461,654 A | * | 10/1995 | Grodzins et al. | 378/45 |
| 6,355,495 B1 | * | 3/2002 | Fujino et al. | 438/18 |
| 7,245,695 B2 | * | 7/2007 | Mazor et al. | 378/44 |
| 2003/0068829 A1 | * | 4/2003 | Giaquinta et al. | 436/173 |

FOREIGN PATENT DOCUMENTS

| | | |
|---|---|---|
| JP | H03-181848 | 8/1991 |
| JP | H08-075683 | 3/1996 |
| JP | H08-145901 | 6/1996 |
| JP | H11-132720 | 5/1999 |
| JP | H11-316201 | 11/1999 |
| JP | 2000-009661 | 1/2000 |
| JP | 2001-196429 | 7/2001 |
| JP | 2002-257756 | 9/2002 |
| JP | 2003-149183 | 5/2003 |
| JP | 2004-170092 | 6/2004 |

* cited by examiner

*Primary Examiner* — Irakli Kiknadze
(74) *Attorney, Agent, or Firm* — Squire Sanders (US) LLP

(57) ABSTRACT

To provide a method and device for testing the size and conductivity of a foreign material adhered to a substrate for a liquid crystal display device, there is provided a method of testing whether a foreign material including a metal element is adhered to a substrate for a liquid crystal display device, the method including a first test step of detecting the size and position of the foreign material adhered to the substrate and a next step of testing whether the foreign material includes the metal element at the position detected in the first test step.

2 Claims, 8 Drawing Sheets

TEST METHOD AND TEST DEVICE

This application is a Continuation Application of U.S. application Ser. No. 12/625,174, filed on Nov. 24, 2009, which was a Continuation of International Application No. PCT/JP2008/052560, filed on Feb. 15, 2008, and which claimed priority to JP Application Nos. 2008-531053, filed on Feb. 15, 2008 and 2008-010300, filed on Jan. 21, 2008, all of which are incorporated by reference.

TECHNICAL FIELD

The present invention relates to a method and device for testing a fine foreign material adhered to a substrate used for a liquid crystal display device before the liquid crystal display device is assembled.

BACKGROUND ART

As is well known in the related art, a liquid crystal display device includes two substrates and liquid crystal sealed therebetween. In the liquid crystal display device, a voltage is applied between electrodes provided on the two substrates to drive the liquid crystal in each pixel, thereby changing the optical property of the liquid crystal. In this way, the liquid crystal display device controls the transmission and shielding of light to display an image on a screen.

In general, a substrate having a glass plate as a base and liquid crystal driving electrodes provided on the base has been used as the above-mentioned substrate. The electrode provided on one of the two substrates is transparent. For example, an ITO thin film is used as the electrode. The electrode provided on the other substrate is changed depending on a liquid crystal driving type. For example, a plurality of transparent electrodes or reflecting electrodes is arranged for each pixel, and a plurality of TFTs is connected to each of the plurality of electrodes.

Color filter films that color display light may be provided on these substrates. The color filter film includes a plurality of coloring films that is arranged so as to correspond to the pixels. For example, red (R), green (G), and blue (B) coloring films are arranged so as to correspond to the pixels. It is possible to display a color image on the screen by using a substrate including the color filter film. The substrate including the color filter film is sometimes referred to as a "color filter".

Therefore, these substrates of the liquid crystal display device are manufactured through a plurality of complicated processes, such as a process of cleaning the surface of a glass plate, a process of forming an electrode film, a process of patterning the electrode film, a TFT forming process, and a color filter film forming process.

Each of the manufacturing processes of the substrate is generally performed in a clean room. Nonetheless, a fine foreign material is likely to be adhered to the substrate during any one of the complicated manufacturing processes. It is considered that the foreign material is caused by dust in the atmosphere of the clean room.

The foreign material adhered to the substrate is likely to damage the surface of an opposite substrate when the liquid crystal display device is assembled. Therefore, the substrate having the foreign material adhered thereto is excluded as a defective product from a liquid crystal display device assembly process and is then corrected, or the glass base is collected and reproduced, or discarded.

However, it has been known that, among the foreign materials, a foreign material with a diameter of 30 μm or more damages the opposite substrate. In addition, a foreign material with a diameter of 20 μm or more is also likely to damage the opposite substrate depending on the kind of liquid crystal display devices manufactured. Therefore, when the size of the foreign material is smaller than the above-mentioned value, the foreign material is ignored during the assembly of the liquid crystal display device without being removed.

However, these foreign materials may include a conductive material. When a substrate having the conductive foreign material adhered thereto is used to assemble the liquid crystal display device, the electrodes of two substrates opposite to each other are short-circuited, making it difficult to normally display an image on the screen. This short circuit occurs even when the diameter of the conductive foreign material is smaller than 20 μm.

When the foreign material adhered to the substrate is a conductive material, the substrate with the foreign material is excluded from the liquid crystal display device assembly process regardless of the diameter thereof. When the foreign material adhered to the substrate is a non-conductive material, it is necessary to exclude the substrate with only the foreign materials with a diameter of more than 20 μm or 30 μm from the liquid crystal display device assembly process. If the substrate having a foreign material with a small diameter adhered thereto is excluded without discriminating conductive and non-conductive materials, non-defective substrates are also excluded, which results in a significant reduction in yield. If the substrate having a foreign material with a small diameter adhered thereto is used during the liquid crystal display device assembly process without discriminating conductive and non-conductive materials, the assembled liquid crystal display device becomes a defective product, which results in an increase in loss.

However, it is very difficult to test whether the fine foreign material is a conductive material. It is considered that the conductive foreign material is also caused by dust in the atmosphere of the clean room. Therefore, the surface of the conductive foreign material is likely to be oxidized. In the liquid crystal display device assembly process, it is assumed that the oxide film on the surface of the foreign material is damaged and a conductive inner part is exposed, which causes a short circuit. Therefore, it is difficult to test whether there is a foreign material during a substrate manufacturing process before the liquid crystal display device assembly process.

In addition, the test needs to be rapidly and effectively performed without delaying the substrate manufacturing process. If it takes a long time to perform the test, the test process becomes a rate-controlling process, and the overall substrate manufacturing process is delayed significantly.

For example, Patent Documents 1 and 2 disclose a method of testing whether a foreign material is adhered to a substrate or the height of the foreign material. However, it is impossible to test whether there is a conductive foreign material using this method.

In addition, Patent Document 3 discloses a method of testing a short circuit between the electrodes after a liquid crystal display device is assembled. However, in this method, the entire short-circuited liquid crystal display device is treated as a defective product.

[Patent Document 1] Japanese Patent Application Laid-Open No. 2004-177192
[Patent Document 2] Japanese Patent Application Laid-Open No. 2006-300892
[Patent Document 3] Japanese Patent Application Laid-Open No. 11-73132

SUMMARY OF THE INVENTION

The invention has been made in order to solve the above-mentioned problems, and an object of the invention is to provide a method of testing the size and conductivity of a foreign material adhered to a substrate. A test object may be two piece of substrate sandwiching a liquid crystal for a liquid crystal display device. In particular, an object of the invention is to provide a method of effectively testing a substrate during a substrate manufacturing process.

Another object of the invention is to provide a test device suitable for the test method.

That is, according to a first aspect of the invention, there is provided a method of testing whether a foreign material including an Fe element or an Al element is adhered to a substrate for a liquid crystal display device in order to select the substrate having the foreign material adhered thereto and remove the substrate during a substrate manufacturing process, the method including:
a first test step of detecting size and position of foreign material adhered to substrates;
and
further steps of
excluding a substrate from which the foreign material with a sufficient size to damage an opposite substrate is detected among the substrates having the foreign materials adhered thereto, which are detected in the first test step,
adjusting position of a test head of a test device to match the position of the foreign material detected in the first step, for the substrates remaining after excluding the substrate,
and
testing only whether the foreign material includes an Fe element or an Al element
wherein,
the adjusting the position of the test head to match the position of the foreign material is performed based on information of coordinates of the position in the first test step,
a camera unit is used to capture an image of position where there is the foreign material,
detailed coordinates of the foreign material are determined from the image,
and
adjusting the position of the test head to match the position of the foreign material is performed based on the detailed coordinates,
and
when the foreign material includes the Fe element or the Al element, the test device determines that the substrate is defective.

As described above, it is very difficult to directly test whether a fine foreign material is a conductive material. From experience, a conductive foreign material adhered to the substrate in the substrate manufacturing process is iron or aluminum. Therefore, in any of the further steps of the invention, it is tested whether a metal element is included in the foreign material, and it is possible to estimate whether there is a conductive material based on whether the metal element is included in the foreign material. In addition, even when the surface of the foreign material is oxidized, it is possible to easily estimate whether there is a conductive material. Therefore, it is possible to effectively and rapidly test the substrate, as compared to the case where it is directly tested whether the fine foreign material is a conductive material.

According to the invention, first, in the first test step, the size of the foreign material adhered to the substrate is detected. When the detected foreign material damages the opposite substrate, it is possible to exclude the substrate as a defective product from the liquid crystal display device assembly process.

For the remaining substrates, that is, the substrates from which a foreign material having a sufficient size to damage the opposite substrate is not detected, it is tested whether the foreign material includes a metal element and then it is estimated whether there is a conductive material in any of the further steps. Therefore, it is possible to effectively and rapidly perform a test process, as compared to the case where it is tested whether there is a conductive foreign material on all the substrates. In addition, since the position of the foreign material is detected in the first test step, it is possible to perform any of the further steps based on the detected position. Therefore, it is possible to improve the efficiency and speed of the test process.

In any of the further steps, it is tested whether a metal element is included in the foreign material, and it is estimated whether there is a conductive material based on whether a metal element is included in the foreign material. Therefore, it is possible to rapidly and effectively perform a test process regardless of whether the surface of the foreign material is oxidized.

Therefore, the method of testing the size and conductivity of the foreign material adhered to the substrate according to the first aspect of the invention can be used in the substrate manufacturing process to effectively and rapidly test a substrate.

An aspect of the invention defines the size of a foreign material that damages an opposite substrate. In the test method according to an aspect, the size is a diameter of 20 µm. In addition, it is preferable that the size be a diameter of 5 µm.

The invention limits the detected metal element to an Fe element or an Al element since a conductive foreign material is generally iron or aluminum, thereby improving the efficiency of detection. In the test method according to any one of the aspects, the metal element is an Fe element or an Al element.

An aspect of the invention provides a method capable of detecting a metal element at a high speed in a non-contact manner. In the test method according to the first aspects, any on of the further steps is based on an X-ray fluorescence spectrometer.

An aspect of the invention provides a method capable of detecting a metal element at a high speed in a non-contact manner. In the test method according to an aspect, any of the further steps is based on an X-ray fluorescence spectrometer.

A detecting method based on the X-ray fluorescence spectrometer radiates X-rays with a short wavelength and high energy to a foreign material, which is a test target, and measures the wavelength and intensity of fluorescent X-rays generated in response to the X-rays. The wavelength of the fluorescent X-ray is peculiar to an element included in the foreign material, and the intensity of the fluorescent X-ray is related to the content of the element. Therefore, it is possible to detect the kind of metal element included in the foreign material and the content thereof by measuring the wavelength and intensity of the generated fluorescent X-ray. According to this method, it is possible to detect the metal element in a non-contact manner. Therefore, it is possible to detect the element at a high speed without physically damaging the surface of the substrate. (In this specification, both words "X-ray fluorescence analysis" and "fluorescent X-ray analysis" are used as an identical word.)

According to the aspects of the invention, the method and device for testing the size and conductivity of the foreign material adhered to the substrate can be used in the substrate manufacturing process to effectively and rapidly test a substrate.

A second aspect of the present invention is a test device of detecting a foreign material including an Fe element or an Al element adhered to a substrate for a liquid crystal display device in order to select the substrate having the foreign material adhered thereto and remove the substrate during a substrate manufacturing process, the test device comprising:
a holding mechanism that holds the substrate for a liquid crystal display device;
a test head including an X-ray fluorescence analysis unit;
a camera unit which captures an image of position where there is the foreign material after position of the camera unit is adjusted so as to match the position of the foreign material based on information of coordinates of the position of the foreign material, the information obtained beforehand;
a detail position adjusting mechanism determining detailed coordinates of the foreign material based on the image;
a moving mechanism which adjust position of the X-ray fluorescence analysis unit to match detailed position of the foreign material determined by the detail position adjusting mechanism;
a testing means which tests only whether the foreign material includes an Fe element or an Al element, based on result of the X-ray fluorescence analysis unit;
a selecting means which selects a substrate with the foreign material of an Fe element or an Al element as a defective; and
a controlling means which controls the holding mechanism, the test head, the moving mechanism and the test means.

Third aspect of the present invention is the test device according to the second aspect,
wherein the information of the coordinates of the position of the foreign material does not include information of coordinates of position of a foreign material with a sufficient size to damage an opposite substrate.

Fourth aspect of the present invention is the test device according to the second aspect,
wherein the information of the coordinates of the position of the foreign material include both information of coordinates of position of a foreign material with a sufficient size to damage an opposite substrate and information of coordinates of position of a foreign material with an insufficient size to damage an opposite substrate,
and
wherein the camera unit which captures the image of the position where there is the foreign material after position of the camera unit is adjusted so as to match the position of the foreign material based on one or both of the information related to the foreign material of the sufficient size and the information related to the foreign material of the insufficient size.

Fifth aspect of the present invention is the test device according to the third aspect,
wherein the sufficient size is a diameter of about 20 μm.

Sixth aspect of the present invention is the test device according to the fourth aspect,
Wherein the sufficient size is a diameter of about 20 μm.

REFERENCE NUMERALS

10: TEST DEVICE
10a: COLOR FILTER TRANSPORT UNIT
11a: HOLDING MECHANISM
11b: LINEAR DRIVING MECHANISM
12: TEST HEAD
13: TEST HEAD MOVING MECHANISM
14: ANALYSIS UNIT
15: DETERMINING UNIT
16: CONTROL UNIT
17: COLOR FILTER
21: X-RAY DETECTOR
22: X-RAY SOURCE
23: FLUORESCENT X-RAY ANALYSIS UNIT
24: CCD CAMERA
25: LENS
26: LAMP
27: CAMERA UNIT
29: FOREIGN MATERIAL DEFECT
31: FOREIGN MATERIAL DEFECT
32: PATTERN PITCH (PITCH OF A PIXEL INCLUDING SUBPIXELS OF R, G AND B)
33: POINT OF INTEREST
34a: COMPARISON POINT 1
34b: COMPARISON POINT 2
35: CAPTURED IMAGE
42: PROCESSED IMAGE
43: INVALID REGION GENERATED BY IMAGE PROCESSING
51: FOREIGN MATERIAL DEFECT
52: POSITION WHERE IMAGE INCLUDING FOREIGN MATERIAL DEFECT IS ACQUIRED AND FIELD OF VIEW
53: POSITION WHERE REFERENCE IMAGE IS ACQUIRED AND FIELD OF VIEW
54: COLOR FILTER
61: FOREIGN MATERIAL DEFECT
62: PROCESSED IMAGE
71: FOREIGN MATERIAL DEFECT

72: POSITION WHERE IMAGE INCLUDING FOREIGN MATERIAL DEFECT IS ACQUIRED AND FIELD OF VIEW
73: POSITION WHERE REFERENCE IMAGE IS ACQUIRED AND FIELD OF VIEW
74: COLOR FILTER
82: PROCESSED IMAGE
83: INVALID REGION GENERATED BY PATTERN MATCHING
84: AMOUNT OF SHIFT OF REFERENCE IMAGE

BEST MODE FOR CARRYING OUT THE INVENTION

Hereinafter, exemplary embodiments of the invention will be described in detail with reference to the accompanying drawings.

Figure 1:
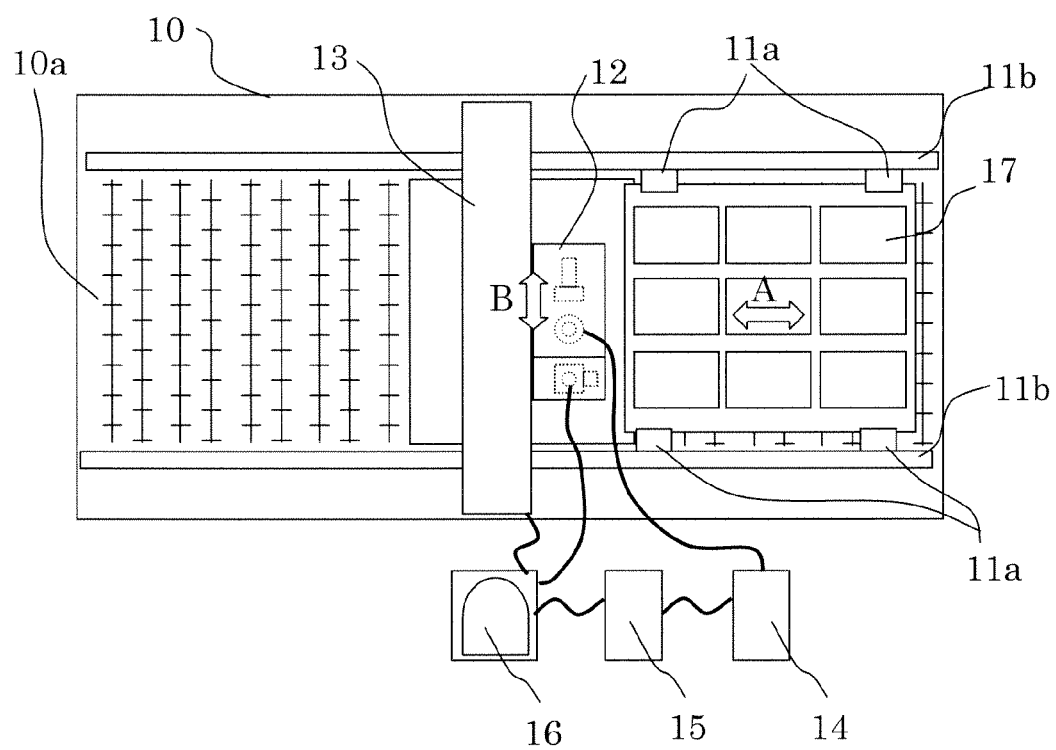
FIG. 1 is a diagram schematically illustrating the upper surface of a test device according to an embodiment of the invention.

FIG. 1 is a diagram schematically illustrating a color filter test device 10 performing any of further steps, as viewed from an upper side. In the following description, a test target is a color filter, but the test target is not limited to the color filter. For example, a substrate that has a glass plate as a base and is used in a liquid crystal display device may be the test target.

Before any of the further steps in the test device 10 according to the embodiment of the invention, the entire surface of a color filter 17, which is a test target, is tested in a first test step, and the position and size of a foreign material defect are specified. Information about the position and size of the foreign material defect can be used in the test device 10.

The color filter 17 carried onto a color filter transport unit 10a of the test device 10 in an upstream process is held and fixed by a holding mechanism 11a such that the surface thereof faces upward. An appropriate number of holding mechanisms 11a are provided on both sides of a transport path of the color filter 17 to hold the ends of the color filter 17. The holding mechanism 11a reciprocates in a straight line along linear driving mechanisms 11b that are provided on both sides of the transport path. In this way, the color filter 17 is transported in the direction of an arrow A in the test device 10.

In order to ensure linear movement, for example, a guide rail may be used as the linear driving mechanism 11b, and a ball screw and a motor may be used as the driving mechanism. A linear motor or a combination of a timing belt and a motor may be used as the driving mechanism.

When the size of the color filter 17 is large, it is generally difficult to stably support the color filter 17 only with the holding mechanism 11a and the linear driving mechanism 11b. Therefore, the color filter transport unit 10a may include a transport roller or an air cushion mechanism, and support the lower surface of the color filter 17. In this embodiment, the air cushion mechanism is used in the vicinity of a main component of the test device, which will be described below, and a transport roller is used in the vicinity of an inlet and an outlet of the test device 10.

A test head 12 is supported above the color filter transport unit 10a by a test head moving mechanism 13, and can be moved in a direction (the direction of an arrow B) orthogonal to the transport direction of the color filter 17. Similar to the linear driving mechanism 11b, the test head moving mechanism 13 may be composed of, for example, a guide rail, a combination of a ball screw and a motor, a linear motor, or a combination of a timing belt and a motor.

In this embodiment, the color filter transport unit 10a transports the color filter 17 in one direction, and the test head 12 can be moved in a direction orthogonal to the transport direction of the color filter 17. In this way, the test head 12 can be moved to an arbitrary position on the color filter 17. However, the color filter transport unit 10a may move the color filter in an XY direction, and the test head 12 may be moved above the color filter in the XY direction.

A control unit 16 controls the driving of the color filter transport unit 10a or the test head moving mechanism 13, based on the size and the coordinates of the position of the foreign material defect on the color filter 17 obtained by, for example, another optical test device in the first test step, to position the test head 12 with respect to the foreign material defect. After the positioning operation, the test head 12 and a test unit (including an analysis unit 14 and a determining unit 15) test a metal element included in the foreign material (which will be described in detail below). The control unit 16 controls the operations of the test head 12, the analysis unit 14, and the determining unit 15, if necessary. In addition, the test head 12 is provided with a fluorescent X-ray analysis unit, which will be described below. The fluorescent X-ray analysis unit detects the metal element included in the foreign material. The size of a spot measured by the fluorescent X-ray analysis unit is significantly smaller than that of the color filter 17. However, since the position of the foreign material defect is detected in the first test step, it is possible to rapidly perform positioning by disposing the fluorescent X-ray analysis unit at the detected position. In addition, the fluorescent X-ray analysis unit can detect the kind of metal element included in the foreign material and the content thereof without contacting the color filter 17. Therefore, it is possible to perform detection at a high speed without physically damaging the surface of the color filter 17.

In this case, the control unit 16 may test all the foreign materials specified by, for example, another optical test device. Alternatively, the control unit 16 may set a predetermined reference to the size of the foreign material and select a foreign material to be tested according to the reference. When a foreign material having a sufficient size to damage the opposite substrate of the liquid crystal display device is detected by, for example, another optical test device, the substrate is excluded from a manufacturing process, or it is corrected. Therefore, in general, a foreign material having a size smaller than a predetermined reference is selected as a test target. As described above, since the size of the foreign material that damages the opposite substrate is equal to or more than 30 μm or 20 μm. Therefore, 20 μm may be set as a reference value, and a substrate including a foreign material with a size equal to or more than the reference value may be excluded from the manufacturing process. In this case, for the remaining substrates, that is, the substrates from which a foreign material having a sufficient size to damage the opposite substrate is not detected, it is tested whether the foreign material includes a metal element. Therefore, it is possible to effectively and rapidly perform a test process, as compared to the case where it is tested whether there is a conductive foreign material on all the substrates. When 5 μm is set as a reference value, it is possible to further reduce the possibility that a defective liquid crystal display device is manufactured.

For example, LAN communication, serial communication, a digital I/O board, and various kinds of recording media such as a floppy (registered trademark) disk, may be used as an input unit that inputs information about the size and position of the foreign material defect to the control unit 16.

Figure 2:
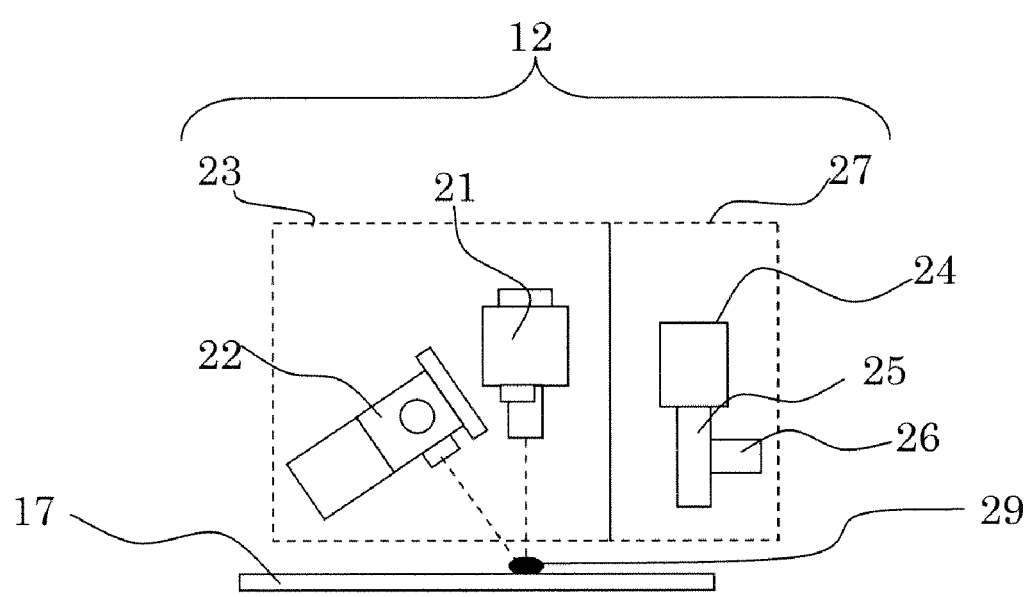
FIG. 2 is a diagram schematically illustrating a main component including a test head of the test device according to the embodiment of the invention, as viewed from the side.

FIG. 2 is a diagram schematically illustrating the main component of the test device 10 according to the embodiment of the invention, as viewed from the side. The test head 12 includes a fluorescent X-ray analysis unit 23 and a camera unit 27.

When the fluorescent X-ray analysis unit is positioned based on information on the position of the foreign material specified by another optical test device, the fluorescent X-ray analysis unit may not be disposed at the position of the foreign material depending on the positioning accuracy of the color filter transport unit 10a and the test head moving mechanism 13. In particular, it is actually difficult to dispose the fluorescent X-ray analysis unit 23 at the position of the foreign material with a size in the range of several tens of micrometers to several micrometers on a color filter having a side with a length of several meters, using the moving mechanism that can move the fluorescent X-ray analysis unit 23 at an arbitrary position on the entire surface of the color filter.

In the test device 10 according to this embodiment, the camera unit 27 including a CCD camera 24, which is an imaging unit, a lens 25, and a lamp 26 is provided in the test head 12. The test head 12 is moved to a position on the color filter 17 where a foreign material 29 to be tested is placed, captures the image of the position where the foreign material 29 is placed, processes the image to extract a foreign material defect, and determines the detailed coordinates of the position of the foreign material 29 from the current position of the camera unit 27 and the position of the foreign material in the image. Of course, when the accuracy of the positioning of the test head 12 to the coordinates of the position of the foreign material is sufficiently high, the camera unit 27 may not be provided in the test head 12.

As shown in FIG. 2, the camera unit 27 may be fixed to the fluorescent X-ray analysis unit 23 and moved integrally therewith. Alternatively, the camera unit 27 may be moved separately from the fluorescent X-ray analysis unit 23.

Then, the fluorescent X-ray analysis unit 23 is moved to the detailed coordinates of the foreign material 29 determined by the camera unit 27. Specifically, the fluorescent X-ray analysis unit 23 is moved to a position where an X-ray source 22 of the fluorescent X-ray analysis unit 23 can radiate X-rays with a short wavelength and high energy to the coordinates of the foreign material 29. Fluorescent X-rays peculiar to an element included in the foreign material 29 are emitted from the foreign material 29 irradiated with the X-rays. Therefore, an X-ray detector 21 detects the fluorescent X-rays.

The X-ray detector 21 transmits information on the wavelength and intensity of the measured fluorescent X-rays to the analysis unit 14. The analysis unit 14 analyzes the kind of element included in the foreign material 29 and the content thereof based on the received information, and transmits the analysis result to the determining unit 15.

The determining unit 15 compares the analysis result with a predetermined threshold value corresponding to the kind of detected metal elements. When any one of the metal elements is more than the threshold value, the determining unit estimates that the foreign material on the color filter is a conductive material, and determines that the color filter is defective. From experience, in general, the conductive foreign material is iron or aluminum. Therefore, the metal element to be detected may be limited to an Fe element or an Al element. In this case, it is possible to improve the efficiency of detection, as compared to a method of detecting all metal elements. In addition, the content of these metal elements is used as the threshold value. However, a numerical value related to the content of the metal elements may be used as the threshold value. For example, instead of the content of the metal element, the intensity of a fluorescent X-ray peculiar to the metal element may be used as the threshold value. For example, the intensity of a fluorescent X-ray peculiar to the Fe element or the intensity of a fluorescent X-ray peculiar to the Al element is measured, and the measured value is compared with a predetermined threshold value. When the measured value is more than the threshold value, it is estimated that the foreign material is a conductive material, and it is determined that the color filter is defective.

When it is determined that the color filter is defective, it is preferable to notify the fact to the operator by displaying various warning messages on the screen of a display device that is provided together with the control unit 16, turning on a warning lamp, or giving the alarm.

X-ray fluorescence spectrometers that are on the market may be used as the X-ray source 22, the X-ray detector 21, and the analysis unit 14.

Figure 3:
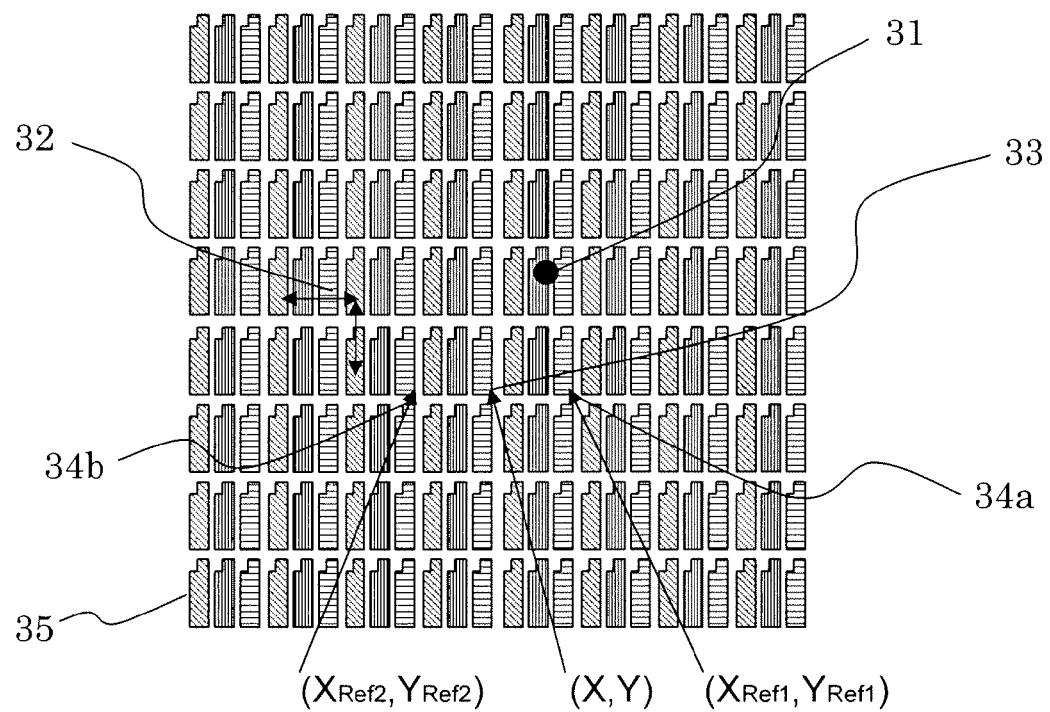
FIG. 3 is a diagram schematically illustrating an example of the image including a foreign material defect captured by a camera unit.

Here, a method of measuring the detailed coordinates of the foreign material 29 using the camera unit 27 will be described. As described above, the color filter 17 includes a color filter film formed on a glass plate. Therefore, for example, red (R), green (G), and blue (B) coloring films are arranged so as to correspond to each pixel. FIG. 3 is a diagram schematically illustrating an example of an image 35 of the color filter 17 captured by the camera unit 27.

In the image 35 shown in FIG. 3, when the camera unit is moved a distance that is the integer multiple of a pattern pitch 32, the same pattern appears on the color filter film. Therefore, a comparison point 34a having the coordinates ($X_{Ref1}$, $Y_{Ref1}$) and a comparison point 34b having the coordinates ($X_{Ref2}$, $Y_{Ref2}$) that are separated from a point 33 of interest having the coordinates (X, Y) by the integer multiple of the pattern pitch 32 are set on the image 35, and image processing represented by the following [Equation 1] is performed on the brightness D(X, Y) of each point of interest to obtain a difference D'(X, Y) between the brightnesses.

$$D'(X,Y)=D(X,Y)-(D(X_{Ref1},Y_{Ref1})-D(X_{Ref2},Y_{Ref2}))/2,$$
$$(\text{where } X: 0\sim X_{max}, Y: 0\sim Y_{max}).\qquad\text{[Equation 1]}$$

However, for simplicity of explanation, FIG. 3 shows a case in which $Y_{Ref1}=Y_{Ref2}=Y$.

Figure 4:
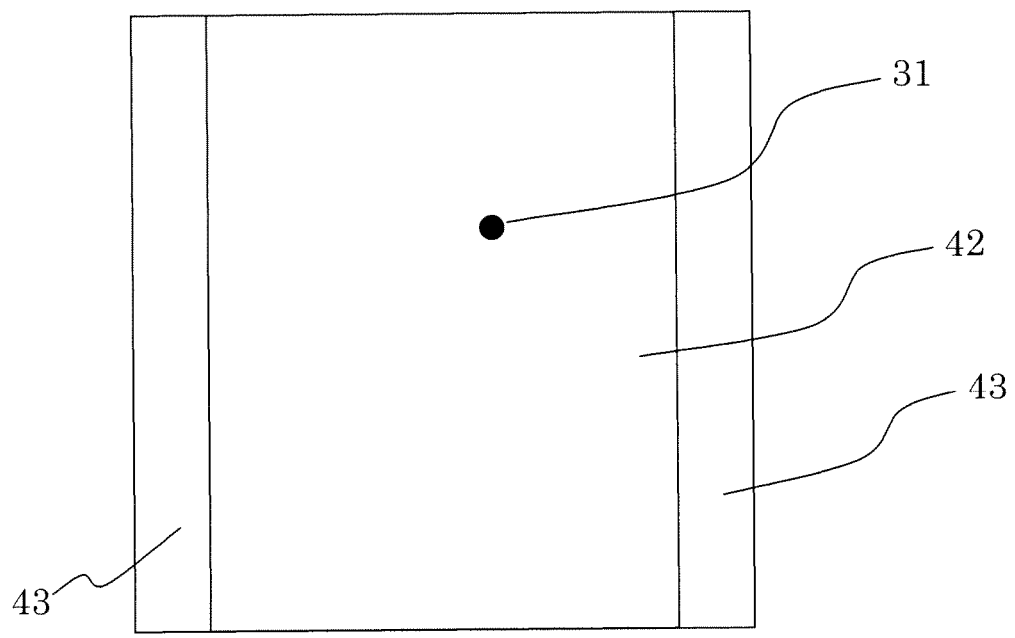
FIG. 4 is a diagram schematically illustrating a defect extracted from the image that has been captured by the camera unit and then subjected to image processing.

FIG. 4 is a diagram schematically illustrating the difference D'(X,Y) between the brightnesses that is obtained by the image processing represented by [Equation 1] as a processed image 42. It is impossible to set a comparison point in left and right regions 43 of the processed image 42, and the left and right regions are invalid regions in which the image processing represented by [Equation 1] cannot be performed. In the region 42 in which the image processing represented by [Equation 1] can be performed, only the coordinates of a foreign material 31 have D'(X,Y) with a large absolute value. Therefore, it is possible to determine the detailed coordinates of the foreign material 31.

Figure 5:
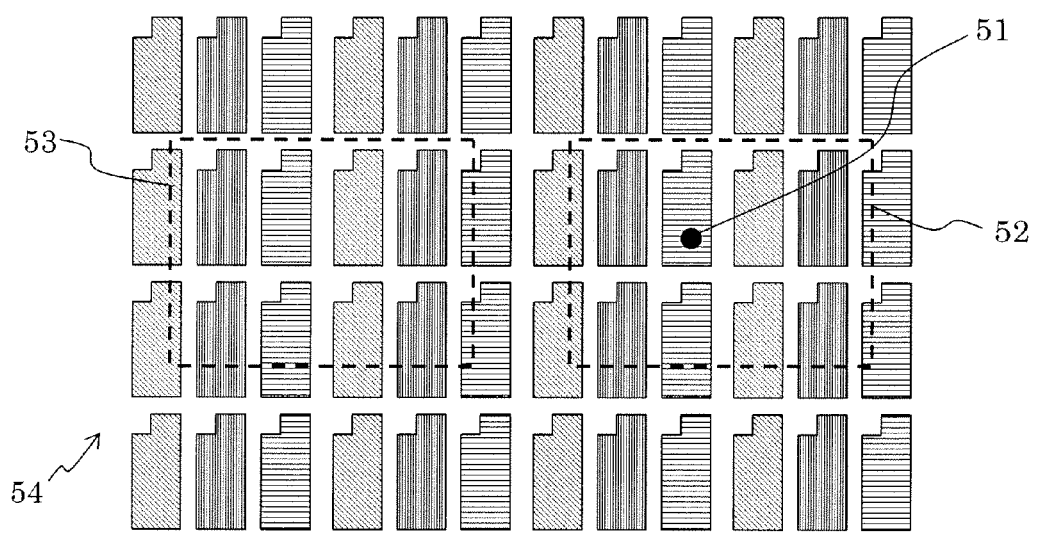
FIG. 5 is a diagram schematically illustrating the position of an image including a foreign material defect captured by the camera unit and the position where a reference image is acquired.
Figure 6:
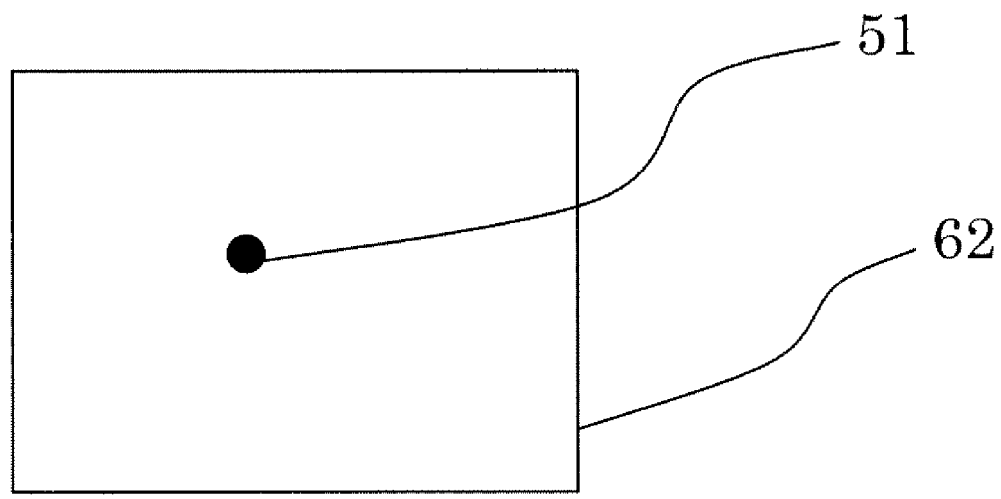
FIG. 6 is a diagram schematically illustrating a defect that is extracted from an image obtained by performing an image difference process on the image including a foreign material defect captured by the camera unit and the reference image.

The above-mentioned method of measuring the detailed coordinates of the foreign material 31 can be applied to a case in which the camera unit 27 can capture the image of a relatively large area. Next, a method of measuring the detailed coordinates of the foreign material 31 when it is difficult to capture the image of a large area with the camera unit 27 will be described with reference to FIGS. 5 and 6.

When data of the defect coordinates to be tested is input to the control unit 16, the camera unit 27 is moved to a position that is separated from a defect position on a color filter 54 by a comparison pitch which is separately input, and captures a reference image 53. Then, the camera unit is moved to the defect position to capture an image 52 of the position that is regarded to have a defect 51. The difference between the two images is calculated to obtain an image 62, and a foreign material defect 51 is extracted. It is possible to determine the detailed coordinates of the foreign material 51 from the current position of the camera unit 27 and the position of the foreign material defect in the processed image 62.

Figure 7:
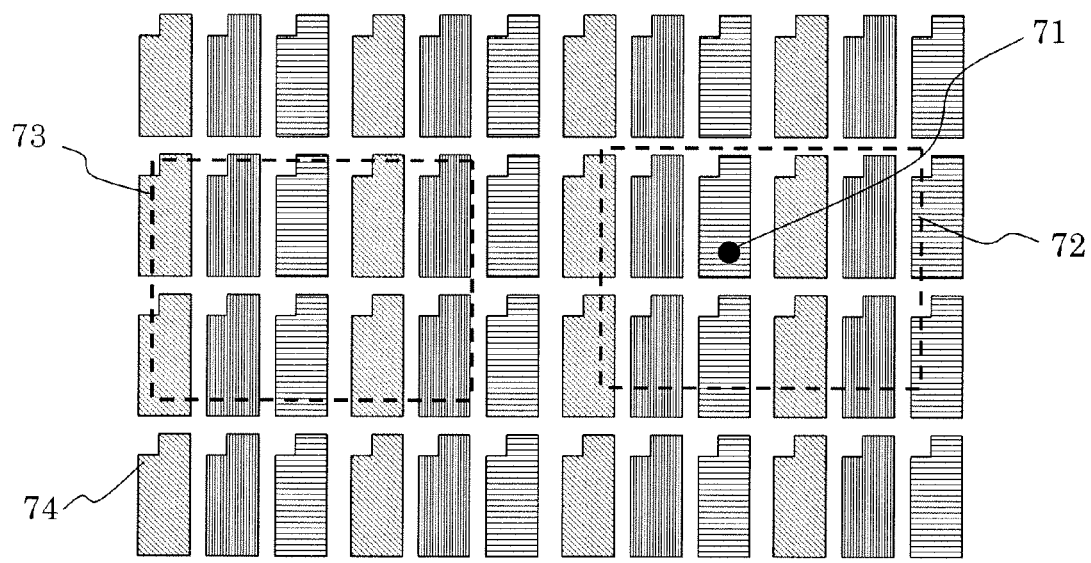
FIG. 7 is a diagram schematically illustrating the position of an image including a foreign material defect captured by the camera unit and the position where a reference image is acquired.
Figure 8:
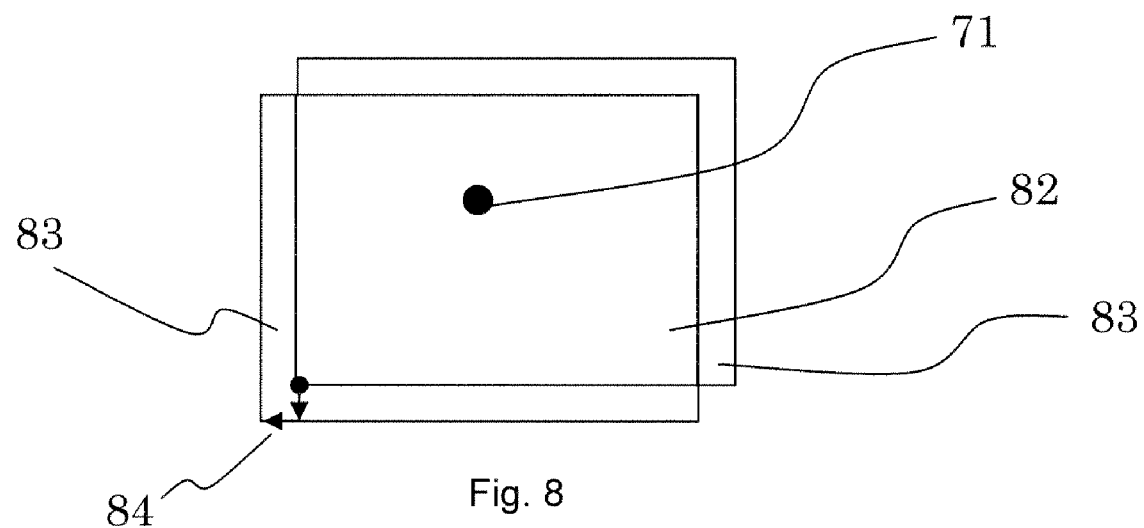
FIG. 8 is a diagram schematically illustrating a defect that is extracted from an image obtained by performing an image difference process on the image including a foreign material defect captured by the camera unit and the reference image.

In this method, when there is a deviation from the pattern of the color filter during the acquisition of the image 52 and the reference image 53, the foreign material defect may not be extracted well. Next, a method of measuring the detailed coordinates of the foreign material 31 when there is a deviation between the image including a foreign material defect and the reference image will be described with reference to FIGS. 7 and 8.

When data of the defect coordinates to be tested is input to the control unit 16, the camera unit 27 is moved to a position that is separated from a defect position on a color filter 74 by a comparison pitch which is separately input, and captures a reference image 73. Then, the camera unit is moved to the defect position to capture an image 72 of the position that is regarded to have a defect 71.

Pattern matching between the two images is performed using the pattern of the color filter 74 to calculate the amount of positional deviation between the two images. Then, the reference image is shifted by the calculated amount of positional deviation, and the difference between the two images is calculated to obtain an image 82. Then, the defect 71 is extracted from the image. It is possible to determine the detailed coordinates of the foreign material 71 from the current position of the camera unit 27 and the position of the foreign material defect in the processed image 82.

In that way, the detailed coordinates of the foreign material adhered to a substrate for a liquid crystal display device are determined, and it is possible to accurately radiate X-rays to the foreign material. Therefore, it is possible to perform accurate and effective fluorescent X-ray analysis. As a result, it is possible to effectively and rapidly test a substrate during a substrate manufacturing process.

EXAMPLES

In the test device having the above-mentioned structure shown in FIG. 1, a color filter was used as a test target and the X-ray source was driven under the conditions of a tube voltage of 100 kV and a tube current of 100 mA to perform a test for a measurement time of 10 seconds. An output of 15,000 cps was obtained from an Fe particle with a diameter of about 10 μm with energy of Fe—Kα rays (cps is a unit indicating the number of X-ray photons measured per second). Under the same conditions, an output of 200 cps was obtained from a resin sphere with a diameter of about 50 μm. Under the same conditions, an output of 180 cps was obtained from a position on the color filter where there was no defect. Then, when a threshold value was set to 1,000 cps, the determining unit could detect and determine the Fe particle with a diameter of about 10 μm.

The invention claimed is:

1. A method of testing whether a foreign material including an Fe element or an Al element is adhered to a substrate for a liquid crystal display device in order to select the substrate having the foreign material adhered thereto and remove the substrate during a substrate manufacturing process, the method comprising:

a first test step of detecting size and position of a foreign material adhered to substrates; and further steps of excluding a substrate from which the foreign material with a sufficient size to damage an opposite substrate is detected among the substrates having the foreign materials adhered thereto, which are detected in the first test step, adjusting position of a test head of a test device to match the position of the foreign material detected in the first step, for the substrates remaining after excluding the substrate, and testing only whether the foreign material includes an Fe element or an Al element wherein, the adjusting the position of the test head to match the position of the foreign material is performed based on information of coordinates of the position in the first test step, a camera unit is used to capture an image of position where there is the foreign material, detailed coordinates of the foreign material are determined from the image, and adjusting the position of the test head to match the position of the foreign material is performed based on the detailed coordinates, and when the foreign material includes the Fe element or the Al element, the test device determines that the substrate is defective.

2. A test device of detecting a foreign material including an Fe element or an Al element adhered to a substrate for a liquid crystal display device in order to select the substrate having the foreign material adhered thereto and remove the substrate during a substrate manufacturing process, the test device comprising:

a holding mechanism that holds the substrate for a liquid crystal display device;

a test head including an X-ray fluorescence analysis unit;

a camera unit which captures an image of a position where there is the foreign material after the position of the camera unit is adjusted so as to match the position of the foreign material based on information of coordinates of the position of the foreign material, the information obtained beforehand;

a detail position adjusting mechanism determining detailed coordinates of the foreign material based on the image;

a moving mechanism which adjust position of the X-ray fluorescence analysis unit to match a detailed position of the foreign material determined by the detail position adjusting mechanism;

a testing means which tests only whether the foreign material includes an Fe element or an Al element, based on result of the X-ray fluorescence analysis unit;

a selecting means which selects a substrate with the foreign material of an Fe element or an Al element as a defective substrate; and a controlling means which controls the holding mechanism, the test head, the moving mechanism and the test means.

* * * * *